United States Patent [19]

Hayase et al.

[11] Patent Number: 5,248,687
[45] Date of Patent: Sep. 28, 1993

[54] PHENYLMETHOXYIMINO COMPOUNDS AND AGRICULTURAL FUNGICIDES CONTAINING THEM

[75] Inventors: Yoshio Hayase, Kameyama; Hideyuki Takenaka, Nabari; Norihiko Tanimoto; Michio Masuko, both of Koka; Toshio Takahashi, Nishinomiya, all of Japan

[73] Assignee: Shionogi & Co., Ltd., Osaka, Japan

[21] Appl. No.: 923,588

[22] Filed: Aug. 3, 1992

[30] Foreign Application Priority Data

Aug. 20, 1991 [JP] Japan .................. 3-207886

[51] Int. Cl.⁵ .................. A61K 31/165; C07D 327/44
[52] U.S. Cl. .................. 514/346; 514/599; 544/335; 544/336; 546/291; 564/74
[58] Field of Search .................. 564/74; 514/599, 346; 546/291

[56] References Cited

U.S. PATENT DOCUMENTS 5,187,170 2/1993 Wingert et al. .................. 514/357

FOREIGN PATENT DOCUMENTS 0254426 1/1988 European Pat. Off.
0398692 11/1990 European Pat. Off.
0477631 4/1992 European Pat. Off.

OTHER PUBLICATIONS

Chemical Abstracts 114:246946a (Jun. 1991).

Primary Examiner—Bernard Dentz
Attorney, Agent, or Firm—Wenderoth, Lind & Ponack

[57] ABSTRACT

There is disclosed a compound of the formula (I):

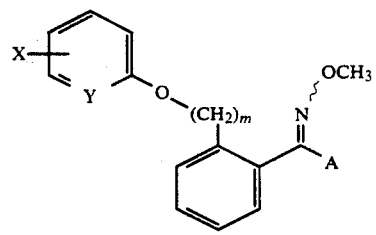

wherein X is a hydrogen atom or 1 to 5 substituents which may be the same or different and are selected from the group consisting of a hydrogen atom, alkyl, alkenyl, alkynyl, optionally substituted phenyl, an optionally substituted heterocyclic group, alkoxy, alkenyloxy, alkynyloxy, optionally substituted phenoxy, mono-, di- or tri-substituted halogenoalkyl and a halogen atom; Y is CH or N; m is 0 or 1; A is a group of the formula:

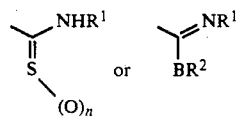

(wherein $R^1$ is a hydrogen atom or alkyl; n is 0 or 1; B is O, S or $NR^3$; $R^2$ and $R^3$ are the same or different and are a hydrogen atom, alkyl, alkenyl, alkynyl, phenyl, benzyl, acyl or phenacyl). There are also disclosed the production thereof and an agricultural fungicide containing the compound as an active component.

4 Claims, No Drawings

PHENYLMETHOXYIMINO COMPOUNDS AND AGRICULTURAL FUNGICIDES CONTAINING THEM

FIELD OF THE INVENTION

The present invention relates to phenylmethoxyimino compounds and agricultural fungicides containing them.

BACKGROUND OF THE INVENTION

The present inventors have found that certain kinds of alkoxyiminoacetamide compounds have excellent fungicidal activities against microorganisms such as *Pyricularia oryzae, Rhizoctonia solani, Pseudoperonospora cubensis* and the like, and have already filed patent applications (EP-A 398692 and Japanese Patent Application No. 2-312519).

After intensive studies, the present inventors have further found that certain novel phenylmethoxyimino compounds, i.e., methoxyiminothioacetamides, methoxyiminoamidines and methoxyiminoimidates, reveal excellent agricultural fungicidal activities from the viewpoints of effectiveness, safety, practical use and the like. Thus, the present invention has been completed.

OBJECTS OF THE INVENTION

The main object of the present invention is to provide novel phenylmethoxyimino compounds useful as agricultural fungicides.

Another object of the present invention is to provide processes for the production of the compounds.

Still another object of the present invention is to provide agricultural fungicides containing the above novel compounds.

These objects as well as other objects and advantages of the present invention will become apparent to those skilled in the art from the following description.

SUMMARY OF THE INVENTION

According to the present invention, there is provided a compound of the formula (I):

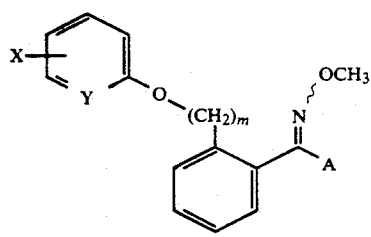

wherein X is a hydrogen atom or 1 to 5 substituents which may be the same or different and are selected from the group consisting of alkyl, alkenyl, alkynyl, optionally substituted phenyl, an optionally substituted heterocyclic group, alkoxy, alkenyloxy, alkynyloxy, optionally substituted phenoxy, mono-, di- or tri-substituted halogenoalkyl and a halogen atom; Y is CH or N; m is 0 or 1; A is a group of the formula:

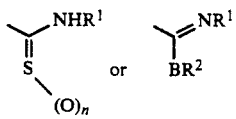

(wherein $R^1$ is a hydrogen atom or alkyl; n is 0 or 1; B is O, S or $NR^3$; $R^2$ and $R^3$ are the same or different and are a hydrogen atom, alkyl, alkenyl, alkynyl, phenyl, benzyl, acyl or phenacyl). The present invention also provides a process for the production thereof and an agricultural fungicide comprising the compound as an active component.

DETAILED DESCRIPTION OF THE INVENTION

Examples of the alkyl represented by X, $R^1$, $R^2$ and $R^3$ in the formula (I) include alkyl having 1 to 6 carbon atoms, preferably 1 to 4 carbon atoms, for example, methyl, ethyl, propyl, isopropyl, butyl, isobutyl, t-butyl and the like.

Examples of the alkenyl represented by X, $R^2$ and $R^3$ include alkenyl having 1 to 6 carbon atoms, preferably 1 to 4 carbon atoms, for example, vinyl, allyl, crotyl and the like.

Examples of the alkynyl represented by X, $R^2$ and $R^3$ include alkynyl having 1 to 6 carbon atoms, preferably 1 to 4 carbon atoms, for example, propargyl, ethynyl, butynyl and the like.

Examples of the alkoxy represented by X include alkoxy having 1 to 6 carbon atoms, preferably 1 to 4 carbon atoms, for example, methoxy, ethoxy, propoxy, isopropoxy and the like.

Examples of the alkenyloxy represented by X include alkenyloxy having 1 to 6 carbon atoms, preferably 1 to 4 carbon atoms, for example, allyloxy, crotyloxy and the like.

Examples of the alkynyloxy represented by X include alkynyloxy having 1 to 6 carbon atoms, preferably 1 to 4 carbon atoms, for example, 2-propynyloxy and the like.

Examples of the halogen atom represented by X include fluorine, chlorine, bromine and iodine.

Examples of the halogenoalkyl represented by X include alkyl which is substituted with at least one halogen atom and has 1 to 6 carbon atoms, preferably 1 to 4 carbon atoms, for example, trifluoromethyl, pentafluoroethyl and the like.

Examples of the optionally substituted phenyl represented by X include phenyl which may be substituted with 1 to 5 substituents selected from the group consisting of the above alkyl, alkenyl, alkynyl, alkoxy, alkenyloxy, alkynyloxy, halogen atom, phenoxy optionally substituted with these substituents, phenyl optionally substituted with these substituents and heterocyclic group optionally substituted with these substituents.

Examples of the optionally substituted heterocyclic group represented by X include heterocyclic groups which may be substituted with 1 to 5 substituents selected from the group consisting of the above alkyl, alkenyl, alkynyl, alkoxy, alkenyloxy, alkynyloxy, halogen atom, phenoxy optionally substituted with these substituents, phenyl optionally substituted with these substituents and heterocyclic group optionally substituted with these substituents. Examples of the heterocyclic ring include a 5 or 6 membered heterocyclic ring containing at least one hetero atom selected from the group consisting of nitrogen, oxygen and sulfur, such as pyridine ring, pyrimidine ring, pyrazine ring, thiazole ring, oxazole ring, isoxazole ring, pyrazole ring, imidazole ring and the like.

Examples of the optionally substituted phenoxy represented by X include phenoxy which may be substituted with 1 to 5 substituents selected from the group consisting of the above alkyl, alkenyl, alkynyl, alkoxy, alkenyloxy, alkynyloxy, halogen atom, phenoxy optionally substituted with these substituents, phenyl optionally substituted with these substituents and heterocyclic group optionally substituted with these substituents.

Examples of the acyl represented by $R^2$ or $R^3$ include acyl having 2 to 7 carbon atoms such as acetyl, benzoyl and the like.

In the formula (I), the substituent X may be at any position of the ring to which X can be attached.

The compound of the formula (I) of the present invention can be an E-isomer, Z-isomer or the mixture thereof due to the configuration of the methoxy group in the methoxyimino group. In the present specification, the both isomers and the mixture thereof are represented by using a wavy line.

The thioacetamide compound of the phenylmethoxyimino compound of the present invention, i.e., the compound of the formula (I'):

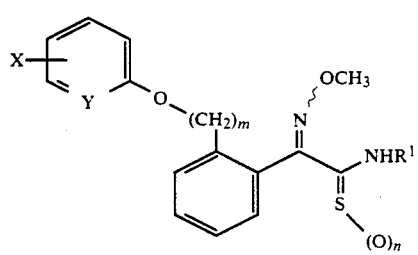

(I')

wherein each symbol is as defined above can be produced, for example, according to the following scheme.

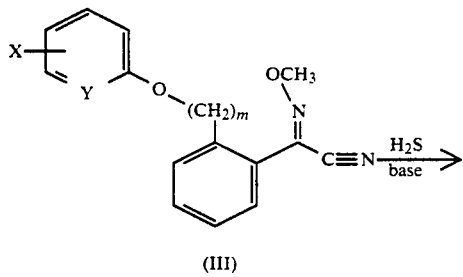

(III)

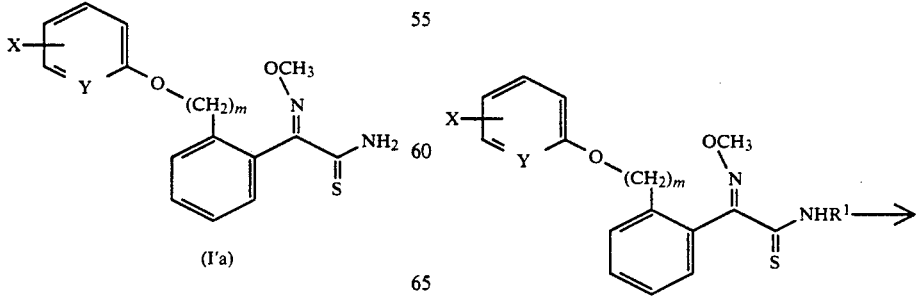

(I'a)

wherein each symbol is as defined above.

That is, the compound (I'a) can be obtained by reacting the corresponding nitrile (III) with hydrogen sulfide at room temperature to 180° C. for 30 minutes to 24 hours in an appropriate organic solvent (e.g., benzene, toluene, chloroform, carbon tetrachloride, dichloromethane, diethyl ether, tetrahydrofuran, dioxane, acetone, methyl ethyl ketone, dimethylformamide, dimethylsulfoxide, etc.) in the presence of a base (e.g., potassium carbonate, sodium carbonate, potassium hydroxide, sodium hydroxide, triethylamine, pyridine, etc.).

Alternatively, the compound (I'b) can be obtained, as shown in the scheme:

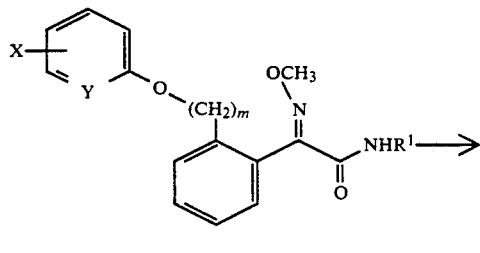

(IV)

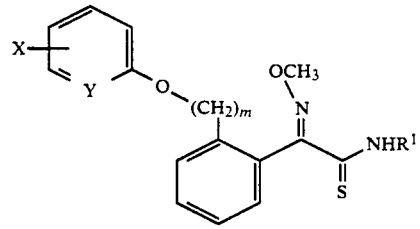

(I'b)

wherein each symbol is as defined above, by reacting the corresponding amide (IV) with phosphorus pentasulfide or Lawesson's reagent [2,4-bis(4-methoxyphenyl)-1,3-dithia-2,4-diphosphethane-2,4-disulfide] [M. P. Cava and M. I. Levinson, Tetrahedron, 41, 5061 (1985)] at room temperature to 150° C. for 30 minutes to 24 hours in an appropriate solvent (e.g., benzene, toluene, tetrahydrofuran, dioxane, chloroform, etc.).

The S-oxide (I'c) of the thioamide can be obtained, as shown in the scheme:

(V)

-continued

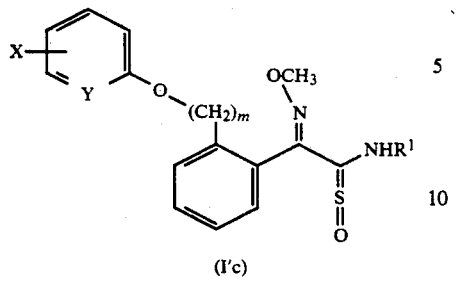

(I'c)

wherein each symbol is as defined above, by oxidizing the corresponding thioamide (V) with an oxidizing agent (e.g., t-butyl hydroperoxide, hydrogen peroxide, peracetic acid, perbenzoic acid, etc.) at 0° to 35° C. for 30 minutes to 24 hours in an appropriate solvent (e.g., methanol, ethanol, butanol, N-methylpyrrolidone, acetic acid, acetone, pyridine, benzene, dimethyl sulfoxide, acetonitrile, etc.).

The imidate and amidine of the phenylmethoxyimino compound of the present invention, i.e., the compound of the formula (I''):

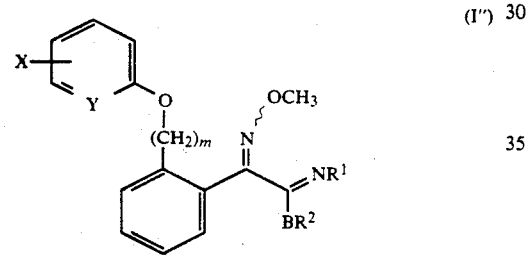

(I'')

wherein each symbol is as defined above, can be synthesized according to the known synthetic methods [S. R. Sandler and W. Karo, "Organic Functional Group Preparations", Vol. 3, Academic Press, New York and London; H. Henecka and P. Kurtz, "Methoden der Organischen Chemie", Houber-Weyl, Vol. VIII, Georg Thieme (1952), pp.697-701; "The Chemistry of Amidines and Imidates" edited by S. Patai, Wiley-Interscience (1975), chap. 4 and chap. 9].

For example, the imidate and amidine can be produced according to the following scheme:

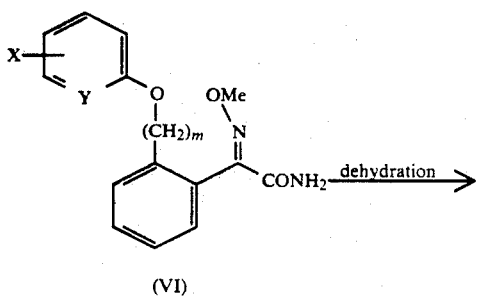

(VI)

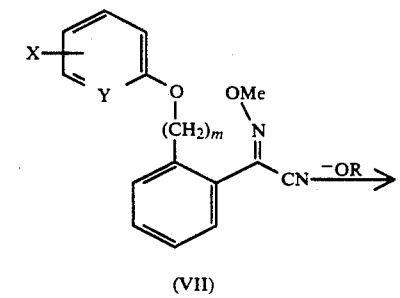

(VII)

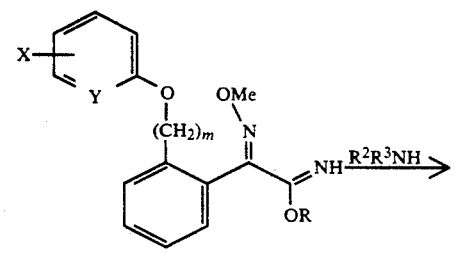

(VIII)

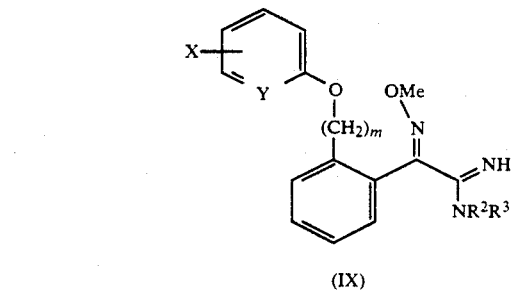

(IX)

wherein R is lower alkyl such as methyl, ethyl or the like, Me is methyl and the other symbols are as defined above.

That is, the amide (VI) is dehydrated by using trifluoroacetic anhydride at −20° to 50° C. for 30 minutes to 24 hours in the presence of a base to obtain the nitrile (VII). Examples of the base include pyridine, tert-amines (e.g., triethylamine, etc.) and inorganic bases (e.g., potassium carbonate, etc.).

Next, the nitrile (VII) is reacted with an alkoxide (e.g., NaOMe, NaOEt, etc.) at −20° to 50° C. for 30 minutes to 24 hours in an appropriate organic solvent (e.g., benzene, toluene, dichloromethane, diethyl ether, tetrahydrofuran, dioxane, dimethylformamide, dimethyl sulfoxide, etc.) to obtain the imidate (VIII).

If necessary, the imidate (VIII) is then reacted with a primary or secondary amine at 0° to 50° C. for 30 minutes to 72 hours in an appropriate organic solvent (e.g., benzene, toluene, dichloromethane, diethyl ether, tetrahydrofuran, dioxane, alcohol, dimethylformamide, dimethyl sulfoxide, etc.) to obtain the amidine (IX).

Alternatively, the imidate and amidine can be obtained according to the following scheme:

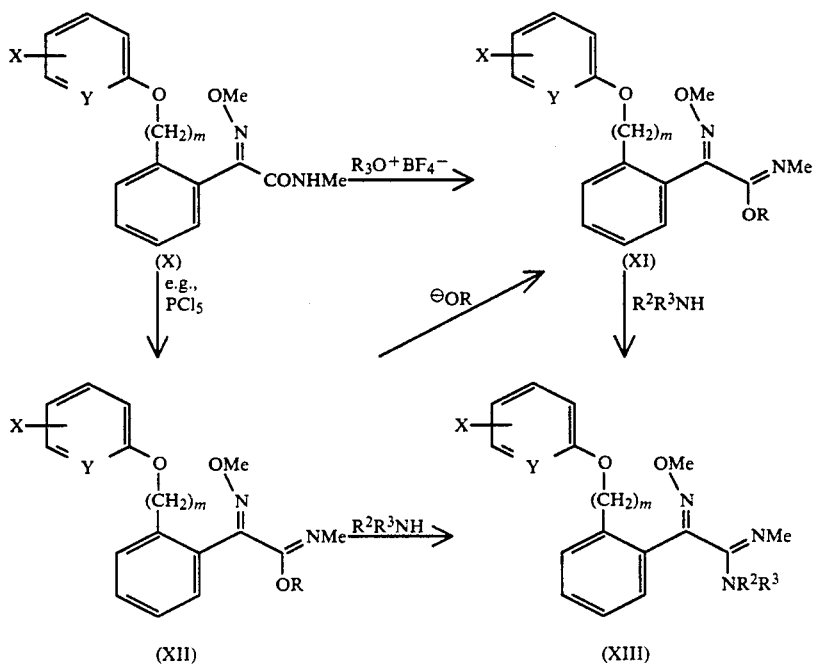

wherein M is a reactive group such as Cl, OAc, OP(-=O)Cl$_2$, OSO$_2$CF$_3$, OCOCF$_3$ or the like, and the other symbols are as defined above.

That is, the amide (X) is reacted with trialkyloxonium tetrafluoroborate at 0° to 5° C. for 1 to 96 hours in an appropriate solvent (e.g., benzene, toluene, dichloromethane, ether, tetrahydrofuran, dioxane, etc.) to obtain the imidate (XI).

The imidate (XI) can be also obtained by reacting the amide (X) with a chlorinating agent (e.g., PCl$_5$, POCl$_3$, SOCl$_2$, COCl$_2$, etc.) at room temperature to 180° C. for 30 minutes to 5 hours to obtain the compound (XII) which is then reacted with an alkoxide in the same conditions as those of the above reaction for converting the nitrile (VII) to the imidate (VIII).

If necessary, the imidate (XI) is then reacted with an amine at −10° to 100° C. in an appropriate solvent (e.g., benzene, toluene, dichloromethane, ether, tetrahydrofuran, dioxane, dimethylformamide, dimethyl sulfoxide, etc.) to obtain the amidine (XIII).

The amidine (XIII) can be also obtained by reacting the compound (XII) with an amine under the same conditions as those of the reaction for converting the imidate (XI) to the amidine (XIII).

The thioimidate (XV) can be produced according to the following scheme:

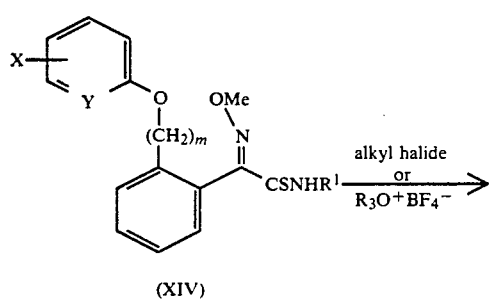

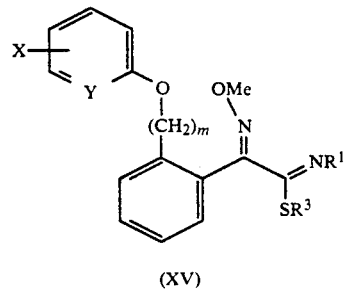

wherein each symbol is as defined above. That is, the thioacetamide (XIV) is reacted with an alkyl halide at −10° to 80° C. in an appropriate solvent (e.g., benzene, toluene, dichloromethane, ether, dioxane, tetrahydrofuran, dimethylformamide, dimethyl sulfoxide, etc.) in the presence of a base (e.g., KOH, NaOH, K$_2$CO$_3$, Na$_2$CO$_3$, NaH, NaOMe, NaOEt, etc.) to obtain the thioimidate (XV). Alternatively, the thioimidate (XV) can be also obtained by subjecting the thioacetamide (XIV) to the same reaction under the same conditions as those of the above reaction for converting the amide (X) to the imidate (XI). As the alkyl halide, there can be used, for example, methyl iodide, ethyl iodide, benzyl chloride or the like.

The nitrile and amide which are used as the starting compounds in the above production processes can be produced readily, for example, according to the method described in the present inventors' EP-A 0468775 and Japanese Patent Application No. 2-312519. The thioacetamide starting compound can be produced readily, for example, according to the above reaction for converting the nitrile (III) into the compound (I′a).

The desired phenylmethoxyimino compounds thus obtained usually exist as a mixture of E-isomer and Z-isomer in terms of the methoxyimino group. The E-isomer and Z-isomer each can be isolated by conventional separation and purification techniques. Therefore, the compound of the present invention include the E-isomer, Z-isomer and a mixture thereof.

As shown in Tables 7 to 9 hereinafter, the phenylmethoxyimino compounds of the present invention show strong fungicidal activities against a wide variety of pathogens on crop plants (e.g., rice, wheat, barley, rye, corn, common millet, millet, buckwheat, soybean, redbean, peanut, cucumber, eggplant, tomato, pumpkin, kidney bean, citrus fruits, grape, apple, pear, peach, etc.) and the like. Specific examples of the pathogen include *Pyricularia oryzae, Rhizoctonia solani, Erysiphe graminis, Sphaerotheca fuliginea, Erysiphe cichoracearum, Phytophthora infestans, Pseudoperonospora cubensis. Peronospora manshurica, Plasmopara viticola, Botrytis cinerea* of vegetables, grape and the like, *Pythium aphanidermatum, Sclerotinia sclerotiorum* of buckwheat, soybean, colza and the like, *Corticium rolfsii* of soybean, redbean, potato, peanut and the like. Therefore, the phenylmethoxyimino compounds of the present invention are useful as agricultural fungicides.

The phenylmethoxyimino compounds of the present invention can be applied to plants by any conventional manner such as atomizing, scattering, spreading or the like. Application may be also made to seeds of plants, soil around plants, soil to be seeded, paddies, water of hydroponic culture or the like. Application can be made before or after the infection of plants with pathogens.

The phenylmethoxyimino compounds of the present invention can be used in the form of a conventional composition or preparation suitable for agricultural fungicides such as solutions, wettable powders, emulsions, suspensions, concentrated liquid preparations, tablets, granules, aerosols, powders, pastes, dusts or the like. These compositions or preparations can be obtained by mixing at least one of the phenylmethoxyimino compounds with an agriculturally acceptable solid or liquid carrier and, if necessary, an appropriate adjuvant (e.g., surfactant, spreader, disperser, stabilizer, etc.) for improvement of dispersibility and other properties of the effective component.

Examples of the solid carrier or diluent include botanical materials (e.g., flour, tobacco stalk powder, soybean powder, walnut-shell powder, vegetable powder, saw dust, bran, bark powder, cellulose powder, vegetable extract residue, etc.), fibrous materials (e.g., paper, corrugated cardboard, old rags, etc.), artificial plastic powders, clays (e.g., kaolin, bentonite, fuller's earth, etc.), talc, other inorganic materials (e.g., pyrophyllite, sericite, pumice, sulfur powder, active carbon, etc.), chemical fertilizers (e.g., ammonium sulfate, ammonium phosphate, ammonium nitrate, urea, ammonium chloride, etc.) and the like.

Examples of the liquid carrier or diluent include water, alcohols (e.g., methanol, ethanol, etc.), ketones (e.g., acetone, methyl ethyl ketone, etc.), ethers (e.g., diethyl ether, dioxane, cellosolve, tetrahydrofuran, etc.), aromatic hydrocarbons (e.g., benzene, toluene, xylene, methylnaphthalene, etc.), aliphatic hydrocarbons (e.g., gasoline, kerosene, lamp oil, etc.), esters, nitriles, acid amides (e.g., dimethylformamide, dimethylacetamide, etc.), halogenated hydrocarbons (e.g., dichloroethane, carbon tetrachloride, etc.) and the like.

Examples of the surfactant include alkyl sulfates, alkyl sulfonates, alkylaryl sulfonates, polyethylene glycol ethers, polyhydric alcohol esters and the like.

Examples of the spreader or disperser include casein, gelatin, starch powder, carboxymethyl cellulose, gum arabic, alginic acid, lignin, bentonite, molasses, polyvinyl alcohol, pine oil, agar and the like.

Examples of the stabilizer include PAP (a mixture of isopropylphosphate), tricresyl phosphate (TCP), tolu oil, epoxidized oil, surfactants, fatty acids and their esters and the like.

The composition of the present invention may contain other fungicides, insecticides, herbicides, fertilizers and the like in addition to the above components.

The composition contains at least one of the phenylmethoxyimino compounds in a concentration of normally 0.1 to 99% by weight, preferably 1 to 60% by weight. The composition can be used as such or in a diluted form. The concentration to be used depends upon a particular purpose, subject and plant to be treated, and it is generally in the range of about 1 to 5,000 ppm. The amount of the active component to be used is generally 1.0 g to 5 kg per hectare.

As described hereinabove, according to the present invention, there are provided novel phenylmethoxyimino compounds and agricultural fungicides containing them.

The following examples and experiments further illustrate the present invention in detail, but are not to be construed to limit the scope thereof.

EXAMPLE 1

Preparation of N-methyl-2-[2-(3-isopropyloxyphenoxymethyl)phenyl]-2-methoxyimino-thioacetamide (Compound No. 12)

Lawesson's reagent [2,4-bis(4-methoxyphenyl)-1,3-dithia-2,4-diphosphethane-2,4-disulfide] (326 mg) and N-methyl-2-[2-(3-isopropyloxyphenoxymethyl)phenyl]-2-methoxyiminoacetamide (580 mg) were suspended in toluene (10 ml). The suspension was stirred at 80° C. for 3 hours. The solvent was distilled off under reduced pressure. The residue was purified by column chromatography on silica gel to obtain the title compound (575 mg).

EXAMPLE 2

Preparation of 2-(2-phenoxyphenyl)-2-methoxyiminothioacetamide S-oxide (Compound No. 4)

2-(2-Phenoxyphenyl)-2-methoxyiminoacetamide (290 mg) was dissolved in acetic acid (5 ml), and 30% aqueous hydrogen peroxide solution (0.13 ml) and sodium acetate (91 mg) were added. The mixture was stirred at room temperature for 4 hours. The reaction mixture was diluted with water and extracted with ethyl acetate. The extract was washed with an aqueous solution of sodium sulfite and aqueous solution of sodium bicarbonate. The solvent was distilled off. The residue was purified by column chromatography on silica gel to obtain the title compound (220 mg).

Likewise, the compounds No. 1 to 3, compounds No. 5 to 11 and compounds No. 13 to 19 shown in Tables 1 to 3 were obtained.

TABLE 1

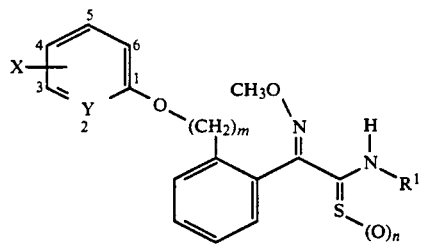

| No. | X | Y | m | R¹ | n | mp (°C.) | ¹H-NMR (CDCl₃) |
|---|---|---|---|---|---|---|---|
| 1 | H | CH | 0 | H | 0 | 124–125 | 3.95(3H, s), 6.88(1H, d, J=7.8), 7.02–7.18(4H, m), 7.23–7.37(5H, m), 8.03(1H, brs). |
| 2 | H | CH | 0 | H | 1 | — | 3.95(3H, s), 6.85(2H, br), 6.88(1H, d, J=7.8), 7.01(2H, d, J=7.8), 7.11(2H, m), 7.21(1H, brd, J=7.8), 7.29–7.39(3H, m). |
| 3 | H | CH | 0 | Me | 0 | 103.5–104.5 | 3.22(3H, d, J=4.9), 3.92(3H, s), 6.86(1H, d, J=7.8), 7.00–7.17(4H, m), 7.25–7.36(4H, m), 8.51(1H, brs). |
| 4 | H | CH | 0 | Me | 1 | 124–137 | 3.27(3H, s), 3.09(3H, s), 6.90(1H, d, J=7.8), 7.02(2H, d, J=7.8), 7.12(2H, m), 7.24–7.39(5H, m). |
| 5 | 3-Me | CH | 0 | Me | 0 | — | 2.29(3H, s), 3.21(3H, d, J=4.9), 3.93(3H, s), 6.81–6.90(4H, m), 7.11–7.19(2H, m), 7.25–7.35(2H, m, 8.50(1H, brs). |
| 6 | 4-Cl | CH | 0 | Me | 0 | — | 3.22(3H, d, J=5.1), 3.92(3H, s), 6.86(1H, d, J=8.3), 6.96(2H, d, J=8.3), 7.20–7.37(5H, m), 8.54(1H, brs). |
| 7 | 3-OCH₂C≡CH | CH | 0 | Me | 0 | 106–108 | 2.50(1H, t, J=2.3), 3.21(3H, d, J=4.9), 3.92(3H, s), 4.62(2H, d, J=2.3), 6.65–7.36(8H, m), 8.50(1H, brs). |
| 8 | 3-OPh | CH | 0 | Me | 0 | — | 3.21(3H, d, J=5.1), 3.88(3H, s), 6.69–6.76(3H, m), 6.92(1H, d, J=8.3), 6.99–7.02(2H, m), 7.13–7.36(7H, m), 8.51(1H, brs). |

TABLE 2

| No. | X | Y | m | R¹ | n | mp (°C.) | ¹H-NMR (CDCl₃) |
|---|---|---|---|---|---|---|---|
| 9 | H | CH | 1 | Me | 0 | 101–101.5 | 3.23(3H, d, J=5.1), 3.95(3H, s), 4.95(2H, s), 6.89–6.96(3H, m), 7.14–7.28(3H, m), 7.34–7.52(3H, m), 8.59(1H, brs). |
| 10 | H | CH | 1 | Me | 1 | 149–151 | 3.31(3H, d, J=5.1), 3.99(3H, s), 4.98(2H, s), 6.89–6.99(3H, m), 7.20(1H, brd, J=7.6), 7.25–7.39(4H, m), 7.47(1H, dt, J=1.4, 7.6), 7.57(1H, d, J=7.1). |
| 11 | 2,5-Me₂ | CH | 1 | Me | 0 | — | 2.21(3H, s), 2.27(3H, s), 3.24(3H, d, J=5.1), 3.96(3H, s), 4.93(2H, s), 6.63(1H, s), 6.65(1H, d, J=7.3), 7.00(1H, d, J=7.3), 7.15(1H, dd, J=7.2, 1.6), 7.33–7.44(2H, m), 7.54(1H, brd, J=7.2), 8.58(1H, brs). |
| 12 | 3-OiPr | CH | 1 | Me | 0 | — | 1.31(6H, d, J=6.1), 3.23(3H, d, J=4.9), 3.95(3H, s), 4.50(1H, sept, J=6.1), 4.91(2H, s), 6.45–6.50(3H, m), 7.09–7.17(2H, m), 7.34–7.44(2H, m), 7.51(1H, d, J=7.1), 8.59(1H, brs). |
| 13 | 3-OiPr | CH | 1 | Me | 1 | — | 1.32(6H, d, J=6.1), 3.30(3H, s), 3.99(3H, s), 4.51(1H, sept, J=6.1), 4.94(2H, s), 6.46–6.51(3H, m), 7.14(1H, d, J=7.6), 7.20(1H, d, J=8.0), 7.36(1H, t, J=7.6), 7.48(1H, t, J=7.1), 7.57(1H, d, J=7.1). |
| 14 | 4-Ph | CH | 1 | Me | 0 | 84–87 | 3.23(3H, d, J=5.1), 3.96(3H, s), 4.99(2H, s), 6.97(2H, d, J=8.8), 7.14–7.54(7H, m), 8.60(1H, brs). |
| 15 | 3-Cl | CH | 1 | Me | 0 | — | 3.24(3H, d, J=4.9), 3.95(3H, s), 4.93(2H, s), 6.81(1H, m), 6.90–6.91(2H, m), 7.14–7.18(2H, m), 7.33–7.40(2H, |

TABLE 2-continued

| No. | X | Y | m | R¹ | n | mp (°C.) | ¹H-NMR (CDCl₃) |
|-----|---|---|---|----|----|----------|----------------|
| 16 | 4-F | CH | 1 | Me | 0 | — | m), 7.47(1H, m), 8.64(1H, brs). 3.25(3H, d, J=5.1), 3.95(3H, s), 4.91(2H, s), 6.83(2H, dd, J=9.3, 4.4), 6.91(2H, dd, J=9.3, 8.3), 7.13(1H, dd, J=6.8, 2.2), 7.36–7.43(2H, m), 7.49(1H, brd, J=6.8), 8.62(1H, brs). |

TABLE 3

| No. | X | Y | m | R¹ | mp (°C.) | ¹H-NMR (CDCl₃) |
|-----|---|---|---|----|----------|----------------|
| 17 | 4-Br | CH | 1 | Me | — | 3.24(3H, d, J=5.1), 3.94(3H, s), 4.92(2H, s), 6.78(2H, d, J=8.9), 7.12(1H, dd, J=6.8, 2.0), 7.33(2H, d, J=8.9), 7.35–7.48(3H, m), 8.65(1H, brs). |
| 18 | 2,4,5-Cl₃ | CH | 1 | Me | — | 3.28(3H, d, J=5.1), 3.97(3H, s), 5.05(2H, s), 7.03(1H, s), 7.12(1H, dd, J=7.1, 1.7), 7.26–7.44(2H, m), 7.44(1H, s), 7.49(1H, brd, J=7.1), 8.10(1H, brs). |
| 19 | 3-Cl, 4-CF₃ | N | 1 | Me | 132–135 | 3.25(3H, d, J=4.9), 3.94(3H, s), 5.29(2H, s), 6.68(1H, d, J=8.5), 7.14(1H, m), 7.37–7.47(2H, m), 7.54(1H, m), 7.81(1H, d, J=8.5), 8.69(1H, brs). |

EXAMPLE 3

Preparation of O-methyl-2-(phenoxyphenyl)-2-methoxyiminoacetimidate (Compound No. 20)

2-(2-Phenoxyphenyl)-2-methoxyiminoacetamide (3.77 g) was dissolved in pyridine (5.53 g). The solution was cooled to 0° C. Trifluoroacetic anhydride (4.40 g) was added dropwise. The mixture was stirred for 2 hours at 0° C., and then diluted with dil. hydrochloric acid and extracted with ethyl acetate. The extract was dried and concentrated to leave a residue, which was purified by column chromatography on silica gel to obtain 2-(2-phenoxyphenyl)-2-methoxyiminoacetonitrile (3.41 g).

The 2-(2-phenoxyphenyl)-2-methoxyiminoacetonitrile (500 mg) was dissolved in methanol (5 ml), and 28% sodium methylate/methanol solution (714 mg) was added. The mixture was stirred at room temperature for 24 hours. The mixture was diluted with water and then extracted with ether. The solvent was distilled off. The residue was purified by column chromatography on silica gel to obtain the title compound, O-methyl-2-(phenoxyphenyl)-2-methoxyiminoacetimidate (398 mg, Compound No. 20) as crystals, mp. 77° C.

EXAMPLE 4

Preparation of N-methyl-2-(2-phenoxyphenyl)-2-methoxyiminoacetamidine (Compound No. 24)

O-Methyl-2-(2-phenoxyphenyl)-2-methoxyiminoacetimidate (398 mg) was dissolved in 30% methylamine/ethanol solution (2 ml). The solution was allowed to stand for 3 days. The excess methylamine and ethanol were distilled off under reduced pressure to obtain the title compound, N-methyl-2-(2-phenoxyphenyl)-2-methoxyiminoacetamidine (Compound No. 24).

EXAMPLE 5

Preparation of N,O-dimethyl-2-[2-(2,4,5-trichlorophenoxymethyl)phenyl]-2-methoxyiminoacetimidate (Compound No. 34)

N-Methyl-2-[2-(2,4,5-trichlorophenoxymethyl)phenyl]-2-methoxyiminoacetamide (603 mg) was dissolved in methylene chloride (5 ml). Trimethyloxonium tetrafluoroborate (444 mg) was added, and the mixture was stirred vigorously at room temperature for 4 days. The mixture was diluted with a saturated aqueous solution of sodium bicarbonate and extracted with methylene chloride. The extract was dried and concentrated. The residue was purified by column chromatography on silica gel to obtain the title compound, N,O-dimethyl-2-[2-(2,4,5-trichlorophenoxymethyl)phenyl]-2-methoxyiminoacetimidate (246 mg, Compound No. 34) as crystals, mp. 97° to 100° C.

EXAMPLE 6

Preparation of N,S-dimethyl-2-[2-(2,5-dimethylphenoxymethyl)phenyl]-2-methoxyiminothioacetimidate (Compound No. 28)

N-Methyl-2-[2-(2,5-dimethylphenoxymethyl)phenyl]-2-methoxyiminothioacetamide (520 mg) was dissolved in methylene chloride (3 ml). Trimethyloxonium tetrafluoroborate (337 mg) was added, and the mixture was stirred at room temperature for a day. The mixture was diluted with a saturated aqueous solution of sodium bicarbonate and extracted with methylene chloride. The extract was dried and concentrated. The residue was purified by column chromatography on silica gel to obtain the desired title compound, N,S-dimethyl-2-[2-(2,5-dimethylphenoxymethyl)phenyl]-2-methoxyiminothioacetimidate (350 mg, Compound No. 28).

Likewise, the compounds No. 21 to 23, compounds No. 25 to 27, compounds No. 29 to 33 and compounds No. 35 to 37 shown in Tables 4 to 6 were obtained.

TABLE 4

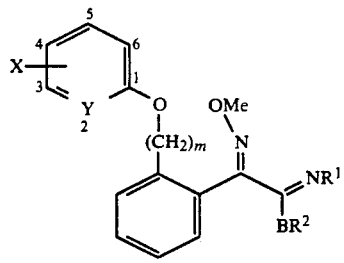

| Comp. No. | X | Y | m | B | R¹ | R² | ¹H-NMR δ (CDCl₃) |
|---|---|---|---|---|---|---|---|
| 20 | H | CH | 0 | O | H | Me | 3.78(3H, s), 3.94(3H, s), 6.93-6.98(3H, m), 7.10(1H, t, J=7.3), 7.17(1H, td, J=7.6, 0.9), 7.26-7.39(4H, m), 7.97(1H, brs). |
| 21 | H | CH | 0 | O | Me | Me | 3.17(3H, s), 3.56(3H, s), 3.92(3H, s), 6.90-6.96(3H, m), 7.08(1H, t, J=7.6), 7.28-7.36(3H, m), 7.54(1H, dd, J=7.6, 1.7). |
| 22 | 4-Cl | CH | 0 | O | H | Me | 3.78(3H, s), 3.93(3H, s), 6.90(2H, d, J=9.1), 6.94(1H, m), 7.17-7.30(2H, m), 7.25(2H, d, J=9.1), 7.36(1H, m). |
| 23 | 4-Me | CH | 0 | O | Me | Me | 2.32(3H, s), 3.18(3H, s), 3.58(3H, s), 3.94(3H, s), 6.85(2H, d, J=8.6), 6.87(1H, m), 7.08-7.14(3H, m), 7.30(1H, dt, J=7.8, 2.0), 7.53(1H, dd, J=7.8, 1.7). |
| 24 | H | CH | 0 | NH | H | Me | 2.92(3H, s), 3.87(3H, s), 6.92(1H, d, J=8.3), 7.00(2H, brd, J=8.1), 7.09(1H, brt, J=7.3), 7.16-7.24(2H, m), 7.28-7.39(3H, m). |
| 25 | H | CH | 1 | O | Me | Me | 3.30(3H, s), 3.65(3H, s), 3.96(3H, s), 5.04(2H, s), 6.92-6.97(3H, m), 7.15-7.43(5H, m), 7.60(1H, d, J=6.6). |
| 26 | 2,5-Me₂ | CH | 1 | O | Me | Me | 2.26(3H, s), 2.28(3H, s), 3.30(3H, s), 3.64(3H, s), 3.97(3H, s), 5.03(2H, s), 6.59-6.68(2H, m), 7.00(1H, m), 7.18(1H, m), 7.24-7.44(2H, m), 7.62(1H, m). |

TABLE 5

| Comp. No. | X | Y | m | B | R¹ | R² | ¹H-NMR δ (CDCl₃) |
|---|---|---|---|---|---|---|---|
| 27 | 2,5-Me₂ | CH | 1 | O | Me | Et | 1.80(3H, t, J=7.1), 2.26(3H, s), 2.28(3H, s), 3.28(3H, s), 3.97(3H, s), 4.05(2H, q, J=7.1), 5.06(2H, s), 6.62(1H, s), 6.68(1H, d, J=7.6), 7.03(1H, d, J=7.3), 7.18(1H, m), 7.31-7.41(3H, m), 7.63(1H, brd, J=7.6). |
| 28 | 2,5-Me₂ | CH | 1 | S | Me | Me | 2.23(3H, s), 2.28(3H, s), 2.56(3H, s), 3.35(3H, s), 3.99(3H, s), 4.99(2H, s), 6.63-6.70(2H, m), 7.00(1H, m), 7.30-7.38(2H, m), 7.42(1H, m), 7.56(1H, m). |
| 29 | 2,5-Me₂ | CH | 1 | O | H | Me | 2.20(3H, s), 2.28(3H, s), 3.86(3H, s), 3.99(3H, s), 4.89(2H, s), 6.57(1H, s), 6.67(1H, d, J=7.4), 7.01(1H, d, J=7.4), 7.14(1H, dd, J=7.4, 1.5), 7.40(1H, td, J=7.4, 1.5), 7.46(1H, td, J=7.4, 1.5), 7.63(1H, brd, J=7.4), 7.95(1H, br). |
| 30 | 2-Cl | CH | 1 | O | Me | Me | 3.33(3H, s), 3.65(3H, s), 3.98(3H, s), 5.14(2H, s), 6.85-6.91(2H, m), 7.34-7.42(3H, m), 7.67(1H, d, J=7.6). |
| 31 | 4-Br | CH | 1 | O | Me | Me | 3.30(3H, s), 3.64(3H, s), 3.96(3H, s), 5.01(2H, s), 6.81(2H, d, J=9.0), 7.16(1H, dd, J=7.0, 2.0), 7.34(2H, d, J=9.0), 7.37-7.43(2H, m), 7.54(1H, brd, J=7.0). |
| 32 | 4-F | CH | 1 | O | Me | Me | 3.32(3H, s), 3.66(3H, s), 3.97(3H, s), 5.04(2H, s), 6.83(1H, brd, J=8.3), 6.90(2H, m), 7.16(2H, m), 7.34-7.41(2H, m), 7.53(1H, brd, J=7.1). |
| 33 | 3-OiPr | CH | 1 | O | Me | Me | 1.32(3H, d, J=6.1), 3.30(3H, s), 3.65(3H, s), 3.96(3H, s), 4.50(1H, sept, J=6.1), 5.01(2H, s), 6.44-6.54(3H, m), 7.11-7.17(2H, m), 7.33(1H, td, J=7.6, |

TABLE 5-continued

| Comp. No. | X | Y | m | B | $R^1$ | $R^2$ | $^1$H-NMR δ (CDCl$_3$) |
|---|---|---|---|---|---|---|---|
| | | | | | | | 1.5), 7.40(1H, td, J=7.6, 1.5), 7.59(1H, d, J=7.6). |
| 34 | 2,4,5-Cl$_3$ | CH | 1 | O | Me | Me | 3.34(3H, s), 3.67(3H, s), 4.00(3H, s), 5.15(2H, s), 6.94(1H, s), 7.13(1H, dd, J=7.3, 1.5), 7.36–7.44(2H, m), 7.47(1H, s), 7.54(1H, brd, J=6.3). |

TABLE 6

| Comp. No. | X | Y | m | B | $R^1$ | $R^2$ | $^1$H-NMR δ (CDCl$_3$) |
|---|---|---|---|---|---|---|---|
| 35 | 2,3,5-Me$_3$ | CH | 1 | O | Me | Me | 2.18(3H, s), 2.25(6H, s), 3.29(3H, s), 3.64(3H, s), 3.97(3H, s), 5.01(2H, s), 6.50(1H, s), 6.62(1H, s), 7.17(1H, dd, J=7.6, 1.2), 7.33(1H, td, J=7.6, 1.5), 7.42(1H, td, J=7.6, 1.5), 7.63(1H, brd, J=7.6). |
| 36 | 4-Ph | CH | 1 | O | Me | Me | 3.18(3H, s), 3.66(3H, s), 3.98(3H, s), 5.08(2H, s), 7.01(2H, d, J=8.1), 7.19–7.55(11H, m). |
| 37 | 4-Cl, 6-CF$_3$ | N | 1 | O | H | Me | 3.89(3H, s), 4.00(3H, s), 5.29(2H, s), 7.13(H, dd, J=7.3, 1.5), 7.39(1H, td, J=7.3, 1.5), 7.45(1H, td, J=7.3, 1.5), 7.61(1H, brd, J=7.3), 7.82(1H, d, J=2.0), 8.18(1H, d, J=2.0). |

The following examples illustrate the agricultural fungicidal composition which can be prepared from the compounds of the present invention. In the examples, all "parts" are by weight unless otherwise indicated.

EXAMPLE 7

A mixture of 2 parts of the Compound No. 2 and 98 parts of talc is pulverized to obtain powders.

EXAMPLE 8

A suspension is prepared by mixing 40 parts of Compound No. 3, 10 parts of sodium lignin sulfonate and 50 parts of water.

EXAMPLE 9

A solution is prepared by mixing 10 parts of Compound No. 8, 1 part of Tween 20 (trade mark) and 89 parts of isopropyl alcohol.

EXAMPLE 10

A wettable powder is prepared by mixing 50 parts of Compound No. 10, 6 parts of sodium alkylbenzenesulfonate, 4 parts of sodium lignin sulfonate and 40 parts of clay and pulverizing the mixture.

EXAMPLE 11

Granules are prepared by mixing 5 parts of Compound No. 13, 90 parts of a mixture of equal amounts of bentonite and talc and 50 parts of sodium alkylbenzene sulfonate, pulverizing the mixture and granulating the pulverized mixture.

EXAMPLE 12

An emulsion is prepared by mixing and dispersing 25 parts of Compound No. 18, 8 parts of polyoxyethylene alkylphenyl ether, 2 parts of sodium alkylbenzene sulfonate and 65 parts of xylene.

EXAMPLE 13

A mixture of 2 parts of the Compound No. 21 and 98 parts of talc is pulverized to obtain a powder.

EXAMPLE 14

A suspension is prepared by mixing 40 parts of Compound No. 23, 10 parts of sodium lignin sulfonate and 50 parts of water.

EXAMPLE 15

A solution is prepared by mixing 26 parts of Compound No. 26, 1 part of Tween 20 (trade mark) and 89 parts of isopropyl alcohol.

EXAMPLE 16

A wettable powder is prepared by mixing 50 parts of Compound No. 30, 6 parts of sodium alkylbenzenesulfonate, 4 parts of sodium lignin sulfonate and 40 parts of clay and pulverizing the mixture.

EXAMPLE 17

Granules are prepared by mixing 5 parts of Compound No. 34, 90 parts of a mixture of equal amounts of bentonite and talc and 50 parts of sodium alkylbenzene sulfonate, pulverizing the mixture and granulating the pulverized mixture.

EXAMPLE 18

An emulsion is prepared by mixing and dispersing 25 parts of Compound No. 35, 8 parts of polyoxyethylene alkylphenyl ether, 2 parts of sodium alkylbenzene sulfonate and 65 parts of xylene.

EXAMPLE 19

A mixture of 2 parts of Compound No. 24 and 98 parts of talc is pulverized to obtain a powder.

EXAMPLE 20

A suspension is prepared by mixing 40 parts of Compound No. 24, 10 parts of sodium lignin sulfonate and 50 parts of water.

EXAMPLE 21

A solution is prepared by mixing 10 parts of Compound No. 24, 1 part of Tween 20 (trade mark) and 89 parts of isopropyl alcohol.

EXAMPLE 22

A wettable powder is prepared by mixing 50 parts of Compound No. 24, 6 parts of sodium alkylbenzenesulfonate, 4 parts of sodium lignin sulfonate and 40 parts of clay and pulverizing the mixture.

EXAMPLE 23

Granules are prepared by mixing 5 parts of Compound No. 24, 90 parts of a mixture of equal amounts of bentonite and talc and 50 parts of sodium alkylbenzene sulfonate, pulverizing the mixture and granulating the pulverized mixture.

EXAMPLE 24

An emulsion is prepared by mixing and dispersing 25 parts of Compound No. 24, 8 parts of polyoxyethylene alkylphenyl ether, 2 parts of sodium alkylbenzene sulfonate and 65 parts of xylene.

Experiments

The following pot experiments show controlling effect of the various compounds of the present invention on plant diseases by foliar treatment.

Experimental Method

In experiments for determination of preventive effect, a liquid sample to be tested was sprayed to test plants. After 24 hours, pathogens were inoculated. The liquid sample was prepared by dissolving the test compound in a small amount of N,N-dimethylformamide and diluting the solution with distilled water containing a spreader to a given concentration. As a control of the known compound, methyl 2-(phenoxyphenyl)-2-methoxyiminoacetate (JP-A 63-23852, EP-A 254426) was used. The percent control was calculated according to the following equation:

$$\text{Percent control (\%)} = \frac{\substack{\text{severity or number} \\ \text{of lesions in untreated} \\ \text{plot}} - \substack{\text{severity or number} \\ \text{of lesions in treated} \\ \text{plot}}}{\substack{\text{severity or number of} \\ \text{lesions in untreated plot}}} \times 100$$

Experiment 1

Controlling effect on *Pyricularia oryzae*

Two-week rice seedlings (var.: AICHIASAHI) were transplanted in plastic cups (each 9 cm in diameter) and cultivated for 2 weeks. The test compound in the form of a solution or suspension was sprayed to the foliage of the rice seedlings. The pathogens were inoculated by spreading a conidia suspension of *Pyriculatia oryzae*, which was cultured in an oatmeal medium, to the foliage. The test plants were kept in a moist chamber (28° C., 100% R.H.) for 24 hours, followed by cultivation in a greenhouse for 5 days. Six days after inoculation, the number of lesions on the leaves of the inoculated plant was assessed, and percent control was calculated.

Experiment 2

Controlling effect on *Rhizoctonia solani*

Two-week rice seedlings (var.: AICHIASAHI) were transplanted in plastic cups (each 9 cm in diameter) and cultivated for 2 weeks. The test compound in the form of a solution or suspension was sprayed to the foliage of the rice seedlings. The pathogens were inoculated by putting mycelia of *Rhizoctonia solani*, which were previously cultivated on the rice bran medium, at the feet of the seedlings together with the rice bran medium. The plants were kept in a moist chamber (28° C., 100% R.H.) for 5 days. The height of the mycelia raised along the leaf sheath was measured, and the percent control was calculated.

Experiment 3

Controlling effect on *Sphaerotheca fuliginea*

Seeds of cucumber (var.: TSUKUBASHIROIBO) were sown in plastic cups (each 9 cm in diameter), followed by cultivation for 2 to 3 weeks. The test compound in the form of a solution or suspension was sprayed on the surface of their first leaves. The pathogen was inoculated by spraying a conidia suspension of *Sphaerotheca fuliginea*, which was cultured on the cucumber leaves, to the leaves. The plants were kept in a greenhouse at 20° C. for 10 days. The infected area on the leaves was observed, and percent control was calculated.

Experiment 4

Controlling effect on *Botrytis cinerea*

Seeds of cucumber (var.: TSUKUBASHIROIBO) were sown in plastic cups (each 9 cm in diameter), followed by cultivation for 2 to 3 weeks. The test compound in the form of a solution or suspension was sprayed to the surface of their first leaves. The pathogen was inoculated by putting mycelial disks (4 mm in diameter) of *Botrytis cinerea*, which was cultured on the potato sucrose agar medium, on the leaf surfaces. The plants were kept in a moist chamber at 20° C. for 2 days. The diameter of the lesions on the leaves was measured, and the percent control was calculated.

Experiment 5

Controlling effect on *Pseudoperonospora cubensis*

Seeds of cucumber (var.: TSUKUBASHIROIBO) were sown in plastic cups (each 9 cm in diameter), followed by cultivation for 2 to 3 weeks. The test compound in the form of a solution or suspension was sprayed on the surface of their first leaves. The pathogen was inoculated by dropping a zoosporangia suspension of *Pseudoperonospora cubensis*, which was cultured on the cucumber leaves, on the under surface (untreated side with the chemical). After inoculation, the plants were kept in a moist chamber at 20° C. for 10 days. The infected area on the leaves was observed, and percent control was calculated.

Results

The results obtained in the above experiments are shown in Tables 7 to 9. In these tables, P.o represents *Pyricularia oryzae*, R.s represents *Rhizoctonia solani*, S.f represents *Sphaerotheca fuliginea*, B.c represents *Botrytis cinerea* and P.c represents *Pseudoperonospora cubensis*. The numbers in these tables represents the percent control (%).

TABLE 7

| No. | P.o | R.s | S.f | B.c | P.c |
|-----|-----|-----|-----|-----|-----|
| 1 | 30 | 0 | 100 | 30 | 0 |
| 2 | 90 | 0 | 90 | 30 | 0 |
| 3 | 90 | 90 | 100 | 70 | 0 |
| 4 | 97 | 50 | 100 | 50 | 70 |
| 5 | 97 | 70 | 100 | 50 | 0 |
| 6 | 97 | 30 | 100 | 50 | 0 |
| 7 | 97 | 30 | 100 | 50 | 0 |
| 8 | 90 | 70 | 100 | 50 | 0 |
| 9 | 70 | 30 | 100 | 70 | 0 |
| 10 | 90 | 30 | 100 | 50 | 100 |
| 11 | 100 | 97 | 100 | 70 | 100 |
| 12 | 97 | 30 | 100 | 50 | 0 |
| 13 | 97 | 50 | 100 | 50 | 100 |
| 14 | 90 | 30 | 100 | 70 | 0 |

TABLE 8

| No. | P.o | R.s | S.f | B.c | P.c |
|-----|-----|-----|-----|-----|-----|
| 15 | 97 | 30 | 100 | 70 | 0 |
| 16 | 90 | 30 | 100 | 50 | 0 |
| 17 | 90 | 30 | 100 | 50 | 0 |
| 18 | 90 | 30 | 100 | 50 | 90 |
| 19 | 100 | 100 | 100 | 70 | 100 |

TABLE 9

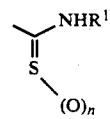

| No. | P.o | R.s | S.f | B.c | P.c |
|-----|-----|-----|-----|-----|-----|
| 20 | 97 | 30 | 100 | 50 | 0 |
| 21 | 97 | 50 | 100 | 70 | 0 |
| 23 | 90 | 30 | 100 | 70 | 0 |
| 24 | 50 | 0 | 70 | 30 | 0 |
| 25 | 97 | 30 | 100 | 30 | 0 |
| 26 | 100 | 100 | 100 | 50 | 0 |
| 27 | 97 | 90 | 100 | 50 | 0 |
| 28 | 100 | 70 | 100 | 50 | 0 |
| 29 | 100 | 90 | 100 | 50 | 0 |
| 30 | 97 | 70 | 100 | 50 | 0 |
| 31 | 97 | 30 | 100 | 50 | 97 |
| 32 | 97 | 50 | 100 | 30 | 50 |
| 33 | 97 | 50 | 100 | 50 | 0 |
| 34 | 97 | 90 | 100 | 70 | 90 |
| 35 | 97 | 90 | 100 | 70 | 0 |
| 36 | 70 | 30 | 100 | 70 | 0 |
| 37 | 100 | 70 | 100 | 50 | 30 |

What is claimed is:

1. A compound of the formula (I):

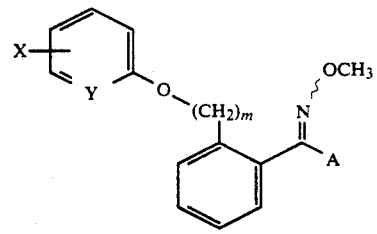

wherein X is a hydrogen atom or 1 to 5 substituents which may be the same or different and are selected from the group consisting of alkyl, alkenyl, alkynyl, phenyl optionally substituted by 1 to 5 substituents selected from the group consisting of the above alkyl, alkenyl, alkynyl, alkoxy, alkenyloxy, alkynyloxy, halogen atom, phenoxy optionally substituted with these substituents, phenyl optionally substituted with these substituents and heterocyclic group selected from the group consisting of pyridyl, pyrimidinyl, pyrazinyl, thiazolyl, oxazolyl, isoxazolyl, pyrazolyl and imidazolyl optionally substituted with these substituents, a heterocyclic group selected from the group consisting of pyridyl, pyrimidinyl, pyrazinyl, thiazolyl, oxazolyl, isoxazolyl, pyrazolyl and imidazolyl optionally substituted by 1 to 5 substituents selected from the group consisting of the above alkyl, alkenyl, alkynyl, alkoxy, alkenyloxy, alkynyloxy, halogen atom, phenoxy optionally substituted with these substituents, phenyl optionally substituted with these substituents and said heterocyclic group optionally substituted with these substituents, alkoxy, alkenyloxy, alkynyloxy, phenoxy optionally substituted by 1 to 5 substituents selected from the group consisting of the above alkyl, alkenyl, alkynyl, alkoxy, alkenyloxy, alkynyloxy, halogen atom, phenoxy optionally substituted with these substituents, phenyl optionally substituted with these substituents and said heterocyclic group optionally substituted with these substituents, mono-, di- or tri-substituted halogenoalkyl and a halogen atom; Y is CH or N; m is 0 or 1; A is a group of the formula:

$$\begin{array}{c} \diagup NHR^1 \\ \diagdown S \\ \diagdown (O)_n \end{array}$$

wherein $R^1$ is a hydrogen atom or alkyl; and n is 0 or 1.

2. A compound according to claim 1, wherein $R^1$ is a hydrogen atom or alkyl having 1 to 6 carbon atoms.

3. An agricultural fungicide composition comprising as an active component the compound according to claim 1 together with an agriculturally acceptable carrier or diluent.

4. A fungicidal method of plants which comprises applying an effective amount of the compound according to claim 1 to the plants.

* * * * *